(12) United States Patent
Champagne

(10) Patent No.: US 7,517,442 B1
(45) Date of Patent: *Apr. 14, 2009

(54) FACILE METHOD AND APPARATUS FOR THE ANALYSIS OF BIOLOGICAL MACROMOLECULES IN TWO DIMENSIONS USING COMMON AND FAMILIAR ELECTROPHORESIS FORMATS

(75) Inventor: James T. Champagne, Vashon, WA (US)

(73) Assignee: Life Technologies Corporation, Carlsbad, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 09/633,172

(22) Filed: Aug. 4, 2000

Related U.S. Application Data

(60) Provisional application No. 60/147,490, filed on Aug. 9, 1999.

(51) Int. Cl.
*G01N 27/26* (2006.01)
(52) U.S. Cl. .................. 204/618; 204/610; 204/644; 204/459; 204/467; 204/548
(58) Field of Classification Search .............. 204/548, 204/455–470, 605–621, 644
See application file for complete search history.

(56) References Cited

U.S. PATENT DOCUMENTS

| | | | |
|---|---|---|---|
| 3,875,044 A | 4/1975 | Renn et al. | |
| 4,094,759 A | 6/1978 | Ruhenstroth-Bauer et al. | |
| 4,130,470 A | 12/1978 | Rosengren et al. | |
| 4,374,723 A * | 2/1983 | Vesterberg | 422/82.01 |
| 4,385,974 A * | 5/1983 | Shevitz | 204/464 |
| 4,415,428 A | 11/1983 | Nochumson et al. | |
| 4,417,967 A | 11/1983 | Ledley | |
| 4,443,319 A * | 4/1984 | Chait et al. | 204/616 |
| 4,666,581 A * | 5/1987 | Itoh et al. | 204/616 |
| 4,693,804 A * | 9/1987 | Serwer | 204/466 |
| 4,746,551 A | 5/1988 | Allen et al. | |
| 5,149,418 A | 9/1992 | Flesher | |
| 5,159,049 A | 10/1992 | Allen | |

(Continued)

FOREIGN PATENT DOCUMENTS

DE 19930253 A1 12/2000

(Continued)

OTHER PUBLICATIONS

Hanash, S.M. et al, "Two-dimensional electrophoresis with immobilized pH gradients in the first dimension: Protein focusing as a function of time". Electrophoresis, 8, 229-234. (1987).*

(Continued)

*Primary Examiner*—Nam X Nguyen
*Assistant Examiner*—Jeffrey T. Barton

(57) ABSTRACT

An ensemble of components and methods are disclosed for utilizing two-dimensional electrophoresis in polyacrylamide or related polymer gels using common, existing and familiar electrophoresis formats and equipment. The disclosed invention makes two-dimensional electrophoresis convenient and easy to use for individuals already using vertical "mini-gel" type systems. The invention discloses the combination of pre-cast disposable gels for both first and second separation dimensions using novel support devices and cassettes that simplify the difficult multiple sample handling and processing steps inherent in ordinary two-dimensional electrophoresis methods. Devices and methods are disclosed in said invention that provide exceptional gel to gel reproducibility.

20 Claims, 9 Drawing Sheets

U.S. PATENT DOCUMENTS

| | | | |
|---|---|---|---|
| 5,209,831 A | 5/1993 | MacConnell | |
| 5,238,651 A | 8/1993 | Chuba | |
| 5,275,710 A * | 1/1994 | Gombocz et al. | 204/461 |
| 5,407,546 A | 4/1995 | Schickle | |
| 5,543,023 A | 8/1996 | Lugojan | |
| 5,593,838 A | 1/1997 | Zanzucchi et al. | |
| 5,699,157 A | 12/1997 | Parce | |
| 5,707,506 A * | 1/1998 | Douthart et al. | 204/622 |
| 5,746,901 A | 5/1998 | Balch et al. | |
| 5,773,645 A | 6/1998 | Hochstrasser | |
| 5,800,690 A | 9/1998 | Chow | |
| 5,827,418 A | 10/1998 | Haven et al. | |
| 5,837,116 A * | 11/1998 | Harrington et al. | 204/606 |
| 5,888,369 A | 3/1999 | Tippins et al. | |
| 5,989,400 A * | 11/1999 | Islam | 204/466 |
| 5,993,627 A * | 11/1999 | Anderson et al. | 204/456 |
| 6,001,233 A | 12/1999 | Levy | |
| 6,013,165 A * | 1/2000 | Wiktorowicz et al. | 204/456 |
| 6,113,766 A * | 9/2000 | Steiner et al. | 204/606 |
| 6,156,182 A * | 12/2000 | Olech et al. | 204/610 |
| 6,398,933 B1 * | 6/2002 | Scott | 204/466 |
| 6,558,522 B1 * | 5/2003 | Williams et al. | 204/459 |
| 6,936,150 B2 | 8/2005 | Rooney et al. | |
| 2003/0015426 A1 | 1/2003 | Rooney et al. | |

FOREIGN PATENT DOCUMENTS

| | | | |
|---|---|---|---|
| WO | WO94/10561 | | 5/1994 |
| WO | WO-1996/04547 | | 2/1996 |
| WO | WO-1998/045693 | | 10/1998 |
| WO | WO 98/57161 | | 12/1998 |
| WO | WO 98/57162 | | 12/1998 |
| WO | WO 99/33550 | * | 7/1999 ................ 204/459 |
| WO | WO 00/31526 | | 6/2000 |
| WO | WO 01/20315 | | 3/2001 |
| WO | WO 02/26773 | * | 9/2001 |
| WO | WO 02/26773 | | 4/2002 |
| WO | WO 02/092200 | | 11/2002 |

OTHER PUBLICATIONS

Amersham Pharmacia Biotech, 2-D Electrophoresis Using Immobilized pH Gradients: Principles and Methods: part 80-6429-60 (Sep. 1998).
BIORAD, PROTEAN® II xi Cell and PROTEAN II xi 2-D Cell Instruction Manual, date not known.
BIORAD, "2-D Electrophoresis: ReadyStrip™ IPG Strips: Part of the ProteomeWorks™ System," date not known.
BIORAD, "Protean II xi multi-cell Instruction Manual: Catalog No. 165-1951," date not known.
BIORAD, "A Flexible, High Throughput Method for 2-D Protein Separations," EG Bulletin 2217, date not known.
BIORAD, "PROTEAN® II xi Cell IPG Conversion Kit Setup Guide," date not known.
BIORAD, "The ProteomeWorks™ System: Now Get More from 2-D," date not known.
BIORAD, "Protein Electrophoresis: Large Precast Gels for 2-D: Part of the ProteomeWorks™ System, Ready Gel Precast Gels for Two-Dimensional Gel Electrophoresis," date not known.
BIORAD, "Protein Electrophoresis: Large Precast Gels for 1-D, Protean® II Ready Gel™ Precast Gels for Single-Dimension Gel Electrophoresis," date not known.
BIORAD, "ReadyStrip™ IPG Strips Instruction Manual: Catalog No. 163-2099," date not known.
Bjellquist et al., "Isoelectric Focusing in Immobilized pH Gradients: Principle, Methodology and Some Applications," Journal of Biochemical and Biophysical Methods 6(4): 317-339 (1982).
Bonnet et al., "Epoxy-Diamine Thermoset/Thermoplastic Blends: Dielectric Properties before, during, and after Phase Separation," Macromolecules 33(10): 3833-3843 (2000).
Bonnet et al., "Epoxy-Diamine Thermoset/Thermoplastic Blends. 2. Rheological Behavior before and after Phase Separation," Macromolecules 32(25): 8524-8530 (1999).
Bonnet et al., "Epoxy-Diamine Thermoset/Thermoplastic Blends. 1. Rates of Reaction before and after Phase Separation," Macromolecules 32(25): 8517-8523 (1999).
Frey et al., "Preparation of Rehydratable Polyacrylamide Gels and Their Application in Ultrathin-layer Isoelectric Focusing", Electrophoresis 7:28-40 (1986).
Gorg et al., "The Current State of Two-Dimensional Electrophoresis with Immobilized pH Gradients," Electrophoresis 21(6): 1037-1053 (Apr. 2000).
Gorg et al., "The Current State of Two-Dimensional Electrophoresis with Immobilized pH Gradients," Electrophoresis 9(9): 531-546 (1988).
Haglund, Herman, "Isolectric Focusing in pH Gradients-A Technique for Fractionalization and Characterization of Ampholytes," Methods of Biochemical Analysis vol. 19, Interscience Publishers, date not known.
Holter et al., "Liquid Crystalline Thermosets Based on Branched Bismethacrylates," Macromolecules 29(22): 7003-7011 (1996).
Islam et al., "A New Approach to Rapid Immobilized pH Gradient IEF for 2-D Electrophoresis," Science Tools from Amersham Pharmacia Biotech 3(1): 14-15 (1998).
Righetti et al, "Isoelectric Focusing in Gels," Journal of Chromatography 98(2): 271-321 (Sep. 25, 1974).
Righetti et al., "Isoelectric Focusing in Immobilized pH Gradients: An Update," Journal of Chromatography B 699(1-2): 77-89 (Oct. 10, 1997).
Righetti et al., "Isoelectric Focusing in Immobilized pH Gradients," Methods in Enzymology 270: 235-255 (1996).
Righetti et al., "Immobilized pH Gradients," Trends in Biochemical Science 13(9): 335-338 (1988).
Yoon et al., "Effect fo Thermal History of the Rheological Behavior of Thermoplastic Polyurethanes," Macromolecules 33(6): 2171-2183 (2000).
"BioRad Laboratories (Life Science catalog)" website Apr. 6, 1997., www.bio-rad.com/5637.html (310.1 892).
Amersham Pharmacia Biotech, "IPGphor IEF System," www.apbiotech.com/stiboasp/showmodule.asp? (Feb. 23, 2001).
BioRad, "PROTEAN.RTM. II xi and XL Multi-cells: Ordering Information," www.bio-rad.com/B2B/BioRad/product/br category.jsp?BV. (Feb. 27, 2002).
BioRad, "PROTEAN II XL Cell for IPG Strips," www.bio-rad.com/B2B/BioRad/product/br category.jsp?BV (Feb. 23, 2002).
Invitrogen Life Technologies, "Xcell SureLock.TM. Mini-Cell: The Most Convenient, Versatile, Mini-Vertical Electrophoresis System," www.invitrogen.com/content. cfm?pageid=3476&cfid=1359647 &cftoken=23915763 (Apr. 18, 2001).
Non-Final Office Action (mailed Dec. 22, 2003) and pending claims, U.S. Appl. No. 10/102,188.
Non-Final Office Action (mailed Sep. 27, 2005) and pending claims, U.S. Appl. No. 10/102,188.
Notice of Allowance (mailed Mar. 24, 2005) and claims, U.S. Appl. No. 10/102,188.
Final Office Action (mailed Sep. 18, 2007) and pending claims, U.S. Appl. No. 10/464,258.
Non-Final Office Action (mailed Jan. 25, 2007) and pending claims, U.S. Appl. No. 10/464,258.
U.S. Appl. No. 10/464,258, Office Action mailed on Sep. 18, 2007.
U.S. Appl. No. 10/464,258, Response to Jan. 25, 2007 Office Action, filed on Jun. 25, 2007.
U.S. Appl. No. 10/102,188, Office Action mailed on Sep. 27, 2004.
U.S. Appl. No. 10/102,188, Response to Sep. 27, 2004 Office Action, filed on Jan. 27, 2005.
U.S. Appl. No. 10/102,188, Response to Dec. 22, 2003 Office Action, filed on May 24, 2004.
EP 02713876, Partial Supplementary EPO Search Report, Oct. 9, 2004.
EP 02713876, Supplementary EPO Search Report, Nov. 26, 2004.
Invitrogen Life Technologies, "Zoom into Fast and Accurate Results: The Zoom IPGRunner System", 2002.
PCT/US02/08438, PCT ISR, Sep. 5, 2002.
WO 2003/106973, PCT Search Report, Dec. 29, 2003.

* cited by examiner

FACILE METHOD AND APPARATUS FOR THE ANALYSIS OF BIOLOGICAL MACROMOLECULES IN TWO DIMENSIONS USING COMMON AND FAMILIAR ELECTROPHORESIS FORMATS This application claims priority from U.S. Provisional Application No. 60/147,490 filed on Aug. 9, 1999.

TECHNICAL FIELD AND INDUSTRIAL APPLICABILITY OF INVENTION

The invention relates to the production of acrylamide or other gels for use in separations of proteins, nucleic acids or other biological materials. The invention further relates to making two-dimensional electrophoresis convenient and easy to use for individuals already using vertical "mini-gel" type systems. The invention discloses the combination of pre-cast disposable gels for both first and second separation dimensions using novel support devices and cassettes that simplify the difficult multiple sample handling and processing steps inherent in ordinary two-dimensional electrophoresis methods.

BACKGROUND OF THE INVENTION

Polyacrylamide gel electrophoresis has become one of the most frequently used techniques for the separation of biological macromolecules such as proteins, nucleic acids and polysaccharides. There is already a wide variety of equipment and methods for many types of high-resolution separation of these biological macromolecules for both analytical and preparative purposes. Two of the most widely used classes of separation methods involve: 1) separating protein molecules according to molecular weight using sodium dodecyl sulfate (SDS) denaturation, often referred to as "SDS-PAGE", and 2) the separation of various types of amphoteric molecules (i.e. molecules with more than one ionizable chemical group) such as proteins using the principle of isoelectric focusing (IEF) on stabilized pH gradients where molecules migrate to a position in an electric field (the isoelectric point) where the pH environment provides a net zero charge on such an amphoteric molecule.

These two arts can be combined wherein a complex mixture of amphoteric molecules are initially focused in a one dimensional pH gradient means, such as a strip or tube of gel, to their component isoelectric points. The focused amphoteric molecules in the one dimensional pH gradient means are then subsequently separated by molecular weight using SDS denaturing electrophoresis in an orthogonal direction to the first dimension. This two-dimensional separation of complex mixtures using polyacrylamide electrophoresis is a powerful but difficult technique. It is often perceived as an art to be reserved for specialists in a biological research organizations who have cultivated the skills to create and implement first dimensional pH gradients in tubes or strips and to successfully equilibrate and transfer the resultant first dimensional gel onto a second dimensional gel using difficult manual transfer and alignment methods.

There is a great demand in everyday research, especially in protein based research, for the high resolution and parallel analysis that is afforded by this two-dimensional analytical approach. If this technique could be made convenient and easy to implement in a format that is familiar to the average laboratory researcher, its use would greatly increase. This is especially true for analysis of small regions of larger two-dimensional gels. The present invention discloses such a facile and convenient method of implementing two-dimensional gel electrophoresis in the popular research electrophoresis format known as a vertical "mini-gel".

SUMMARY OF THE INVENTION

The method provides for the pre-casting and partial dehydration of a plurality of first dimensional pH gradient isoelectric focusing gels cast onto a semi-rigid support in separate parallel discontinuous strips. Each isoelectric focusing gel is provided with an immobilized, and often a titrated acrylamido-buffered, pH gradient or carrier ampholyte generated pH gradient, on said semi-rigid support. The spacing of each of the parallel discontinuous strips matches the standardized conventional multi-well pipettor spacing of about 9 mm on center. In a preferred embodiment of the present invention, the length of the strips is about 8-12 cm, the width is about 3-5 mm and the thickness when fully hydrated is about 0.2-1.0 mm.

Additionally, a molded tight fitting manifold with a plurality of laminar spaces corresponding to each pre-cast strip is provided for the absorption, re-hydration, sample loading and subsequent isoelectric focusing of said strips. The laminar spaces are preferably the same size and shape as the pre-cast isoelectric focusing strips, with a depth slightly greater than the thickness of the isoelectric focusing strip when fully hydrated. The semi-rigid support backing of each strip fits into said manifold as a unit such that each gel strip is sealed and isolated from the other strips in a separate laminar space forming a gel strip-manifold assembly.

The manifold also provides for a sealed laminar void space running the length of each gel strip adjacent to the face of each partially dehydrated gel, which can be filled with a fluid medium. The fluid medium is adsorbed into the partially dehydrated gel so as to hydrate it. In a preferred embodiment, the manifold is molded from elastomeric or semi-elastomeric polymers including but not limited to polysiloxanes, polyisoprenes, polyisobutylenes and polysulfides. Other elastomeric polymers which have physical properties that provide for the easy and tight seal of the semi-rigid (support onto the manifold surface would suffice.

Each laminar void space, with its partially dehydrated isoelectric focusing gel, forms a tight fitting sample loading space adjacent to the gel. In a preferred embodiment, a reclosable, opposing pair of ports are molded into the manifold at the top and bottom of each laminar space. A fluid medium, which can contain either buffer or the sample to be analyzed or separated, is introduced into said laminar void space by opening the ports at the top and bottom and filling the laminar void space through one port, while allowing venting of air or buffer through the other port on the opposite end of the laminar void space. When the fluid medium is fully introduced, both top and bottom ports are reclosed. The opening of these ports can be performed by any hollow tube like dispensing means of proper diameter to fit within the port.

In a further preferred embodiment, the reclosable ports are molded into the elastomeric manifold so they can be opened when a pipette or other sample-loading device is used to introduce the sample, or when used to vent entrained air from the port. The opening is accomplished when the pipette or other sample-loading device is inserted, pushing the channel open. As said pipette or other loading device is removed from the elastomeric manifold, the port opening collapses against itself to form a tight fitting seal.

A diagonal support stand is provided in the present invention to hold the gel strip-manifold assembly for the introduction and incubation of said fluid media through the bottom port of each laminar space and to allow for the venting of entrained air through the top port. The 9-mm spacing provides for convenient simultaneous sample loading with a commonly used 8 or 1-2 place pipettor (Gilson). A sample can then be introduced into the isoelectric focusing gel by adsorption into and re-hydration of the gel while being incubated in the said gel strip-manifold assembly.

Once the sample is fully absorbed into the isoelectric focusing gel strip, the gel strip-manifold assembly is flushed with water to remove unabsorbed fluid. The manifold assembly is then mounted into a standard vertical "mini-gel" electrophoresis apparatus that has an upper and lower reservoir and a means of introducing an electric field through the isoelectric focusing gel from one end of the gel to the other. This vertical "mini-gel" electrophoresis apparatus can be either be constructed for this purpose or can be purchased at a variety of laboratory supply houses (Bio-Rad, Hoefer Scientific, etc.) and adapted for use with any of the conventional designs popular in research laboratories using this electrophoresis format.

Following isoelectric focusing, said manifold is then used with the vertical or diagonal support stand for in situ equilibration of the completed first dimensional isoelectrically focused gel, using buffer conditions required for the subsequent second dimensional separation. Typically these second dimension separation conditions require the rapid diffusion into the gel strip of denaturing and reducing reagents, for example, but not limited to sodium dodecyl sulfate detergent and dithiothreitol, along with other reagents in one or more equilibration stages. Said denaturing and reducing reagents are introduced through the same reclosable ports in the same fashion as was used for introduction of the sample prior to isoelectric focusing.

Pre-cast second dimension gradient gels of relatively uniform dimension, concentration or pore size capable of being contained in compatible molded cassettes are also provided in the present invention. Said cassettes having a surface mounted horizontal opening or port designed to accept a single fully equilibrated isoelectric focusing strip near the top of said second dimension gel. The horizontal opening or port is able to seal said isoelectric focusing strip to the second dimension gel with flat surface to flat surface contact. Said seal also isolates said strip from the electrolyte chamber such that the second dimension gel provides an electrical field vector which only runs vertically through the mated first and second dimension gels and parallel to the face of each gel in the manner usually afforded in vertical "mini-gels".

In a preferred embodiment, a molded elastomeric seal designed to accept the individual first dimension strip and isolate it from the electrolyte reservoir provides this sealing function. Such pre-cast second dimension cassettes may be adapted to function in existing brands of "mini-gel" apparatus or they may be designed to function in custom-built "mini-gel" apparatus.

It is often desirable to remove first dimension gel strips or tubes from the second dimension gel after the sample has completely migrated out of the first dimension gel and into the second dimension gel. It is also desirable for the path of the electrical conductivity to bypass the point of contact between the first and second dimension gel. This bypass minimizes streaking from poorly solubilized residual components on the surface of the second dimension gel. Provision is provided for this in the way of a tab or handle means on the horizontal port or seal such that the seal and first dimensional strip can be removed following de-energizing the apparatus. After de-energizing, the removal of the first dimension gel is accomplished without disassembly or emptying of the electrolyte solutions in the reservoirs. Following removal of the seal and first dimension gel, the apparatus is re-energized and the second dimension gel is run to completion with the electrical path running through the now open horizontal port, thus limiting the time without electric power to a minimum.

Therefore, it is an object of the present invention to provide an apparatus which facilitates two-dimensional gel electrophoresis.

Another object of the invention is to reduce handling and movement of the gel, reduce operator exposure to buffers and samples and improve test result reliability.

Another object of the invention is to provide an apparatus to carry out horizontal as well as vertical movement of sample molecules without touching the gel.

DETAILED DESCRIPTION OF A PREFERRED EMBODIMENT OF THE INVENTION

Examples of two-dimensional electrophoresis procedures for which the apparatus is well-suited are set forth in an article entitled "Analytical and Micropreparative Two-Dimensional Electrophoresis of Proteins" by M. G. Harrington, D. Gudeman, T. Zewert, M. Yun, and L. Hood (METHODS: A Companion to Methods in Enzymology, Volume 3, No. 2, October pp. 98-108, 1991). The contents of this reference, along with all of the references cited in the article are hereby incorporated by reference.

The First Dimensional Gel Strips and Semi-Rigid Support

Figure 2:
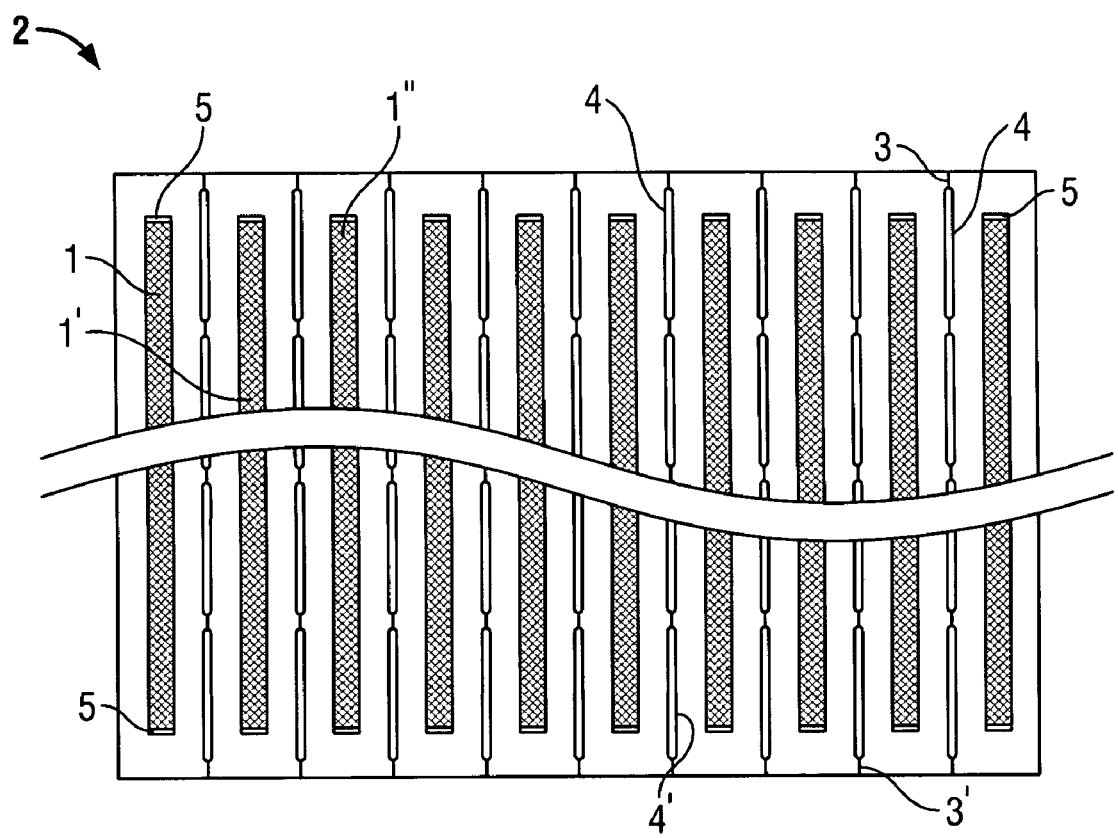
FIG. 2 shows a schematic representation of the details of a semi-rigid support on which a plurality of parallel first dimensional gel strips are cast with compositions allowing for pH gradients to form and allowing for convenient further processing.

In a preferred embodiment shown in FIG. 2, pre-cast polyacrylamide or related pH gradient gel strips (1) are polymerized on and covalently attached to a semi-rigid support (2) such that the gel strips, which are typically about 3-5 mm wide, are spaced at about 9 mm on center with around a 4-6 mm wide space between them and a length of about 80-120 mm. The pre-cast gradient gels can be cast in a discontinuous mold that allows for the introduction of both uniform and gradient variable compositions running the length of the gel. Said semi-rigid support (2), may typically be composed of, but is not limited to, 100-200 micron thick polyester, polymethacrylate or polycarbonate film that has been surface treated to provide a continuous or discontinuous hydrophilic reactive surface that will bind the gel polymer by covalently integrating into the gel matrix. An example of such film is the polyacrylamide support film known as Gel Bond™.

Said semi-rigid support is provided, prior to casting, with die cut perforations (3) and registration holes (4) between each parallel gel strip such that individual strips can be tightly held yet quickly separated from one another by snapping or cutting them off. Said semi-rigid support is also provided with a die cut rectangular hole (5) preferably about 0.5 mm high by the width of the subsequent gel (around 3-5 mm) and located at the extreme top and bottom ends of the gel casting space. These holes provide an electrical connection for the first dimension gel strip through said semi-rigid support to the electrolyte reservoirs without substantial loss of gel support or dead space on the gel.

The polyacrylamide or other gel used in the first dimensional strips can vary in both concentration and composition to provide a wide variety of pH gradient ranges, and denaturing or non-denaturing conditions. Some of these compositions can include but are not limited to chaotropic reagent denaturation such as 6-9M urea, chemically reduced conditions, narrow or broad range carrier ampholytes or immobilized acrylamido pH gradients co-polymerized into the gel.

It is desirable to provide the average laboratory researcher with many overlapping pH ranges and molecular weight ranges that allow them to choose a region that contains two-dimensionally separated proteins of predetermined individual interest. This "window" on one region of the overall two-dimensional grid simplifies the analysis when one is not necessarily interested in exploration of unknown effects and unknown target molecules.

The Isolating Manifold

Figure 1:
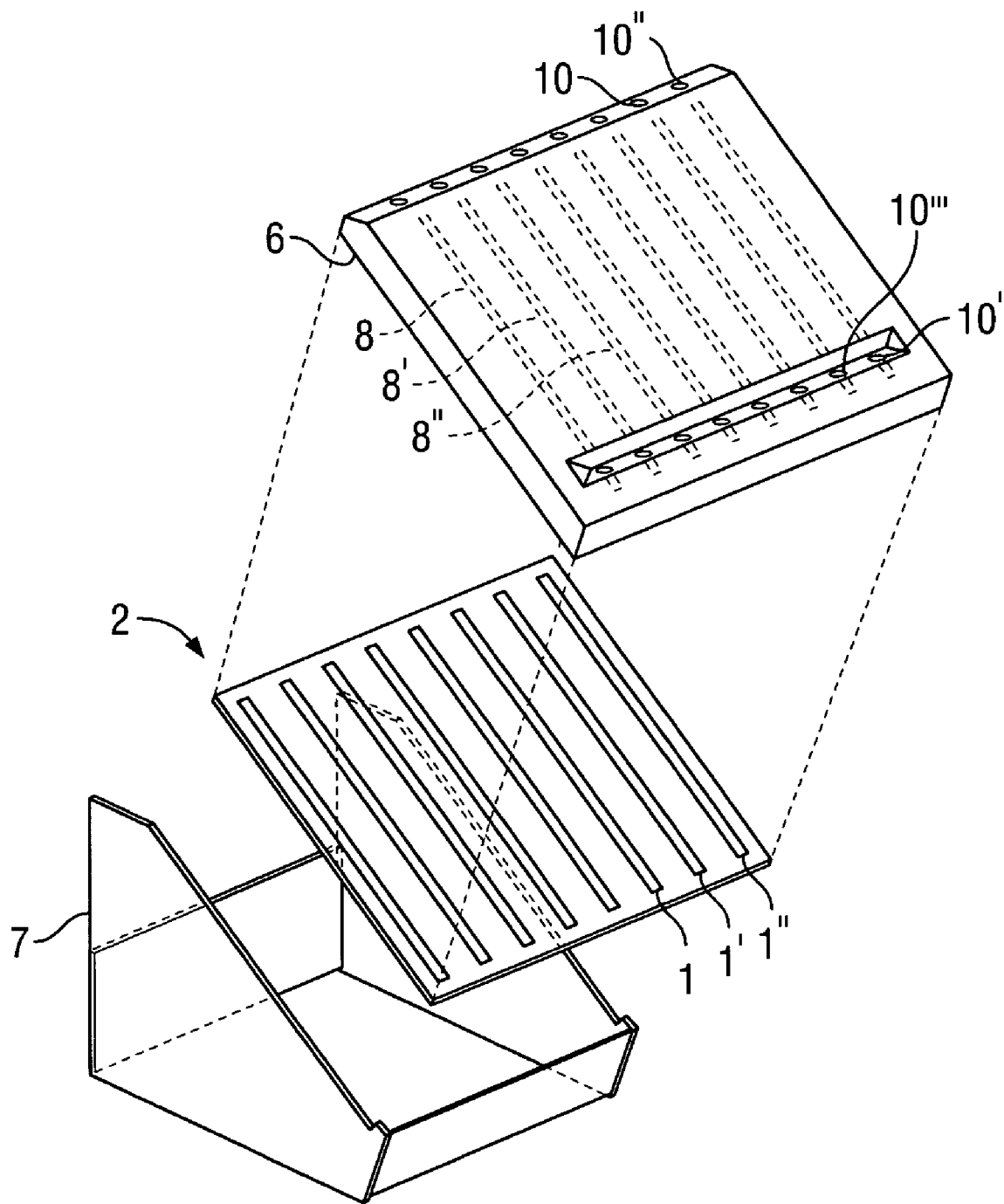
FIG. 1 shows a schematic representation in an exploded isometric view of the various components of the method used for the loading, sample absorption and subsequent re-equilibration of samples to be analyzed using the preferred embodiment of the present invention.

A preferred embodiment shown in FIG. 1 comprises a manifold (6) molded of elastomeric materials such that it can be stretched and mounted onto a more rigid support stand (7), standard gel clamping device or glass plate. Said manifold (6) is provided with a plurality of parallel rectangular channels (8) at around 9 mm on center on the face that is opposite of the mounting face. These rectangular channels are the width and length of the corresponding first dimension gels (1) and have a depth that provides for a very small laminar void space running the length of the gel when the gel is fully hydrated and at its standard thickness. In a preferred embodiment, this laminar void space would be in the order of about 10% to 20% of the standard thickness of the gel.

The face of the manifold-(6) with said channels (8) is further provided with registration tabs (9) between the individual gels along the perforation line that push through corresponding die cut registration holes (4) in the semi-rigid support (2), and also have a perimeter ridge to snap and hold the semi-rigid support (2) tightly in place against the manifold (6). The number of registration tabs is as required to completely seal each channel from the others and from the outside, taking advantage of the properties of elastomeric polymers to seal against smooth surfaces when slight pressure is applied perpendicular to the surface.

Figure 3A:
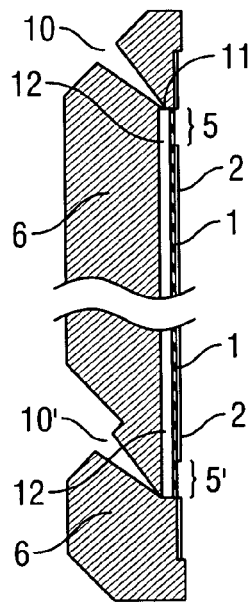
FIG. 3A is a schematic cross sectional representation of the details of an isolating manifold that allows said semi-rigid support shown in FIG. 2 to form individual and isolated sample loading laminar spaces when assembled with said isolating manifold.
Figure 3B:
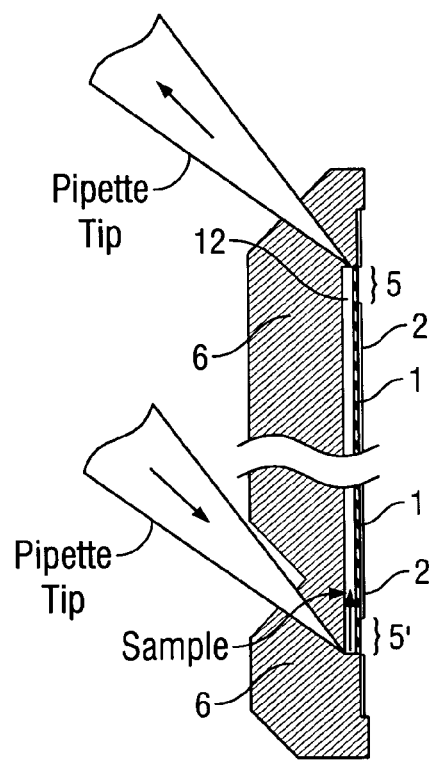
FIG. 3B shows the introduction of fluid media such as samples or equilibration solutions through a reclosable port.
Figure 3C:
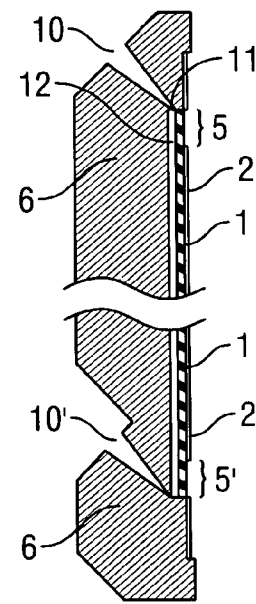
FIG. 3C shows the sealed absorption of the sample into gel strips.

On the opposite side of the elastomeric manifold, at the extreme top and bottom of each gel channel (8), a conical shaped venting or loading port (10) is molded into the manifold (6) corresponding to the shape of a disposable pipette tip of the type commonly found in biological research laboratories (such as Gilson®, or Pipetteman®)(FIG. 3A). At the bottom of said venting or loading ports (10) is a collapsible channel (11) that connects each conical port to the face of the corresponding void space away from the gel when the semi-rigid support and gel is in place. Said collapsible channel (11) is molded into the elastomeric manifold at the time of its polymerization or it is cut through between the conical port (10) and the void space after polymerization of the elastomeric manifold. In a preferred embodiment, the cross section of said connecting channel (11) is very flat (typically about 1-2 mm wide×0.1 mm or less high). Said channel (11) is also designed so as to be able to be pushed open when a disposable plastic pipette tip is inserted into the conical port (FIG. 3B) thereby affording a fluid path into the connected void space on the opposite side of the manifold. This connecting channel is further designed to collapse FIG. 3C and reform a tight fluid seal between the conical port and the void space when the disposable plastic pipette tip is removed.

Said conical ports (10) are oriented to be vertical or nearly vertical when the gel strip manifold assembly is mounted on the support stand used for loading and incubating the samples. This orientation allows for loading of the samples through the bottom conical port on each gel channel by displacement means while pipette tips inserted in the top conical port on each gel channel allow for venting of entrained air or other lower density fluid than the fluid being introduced. In a preferred, embodiment, a support stand (7) for the manifold supports the manifold (6) at a diagonal angle with the conical ports being vertical (FIG. 2).

Figure 4A:
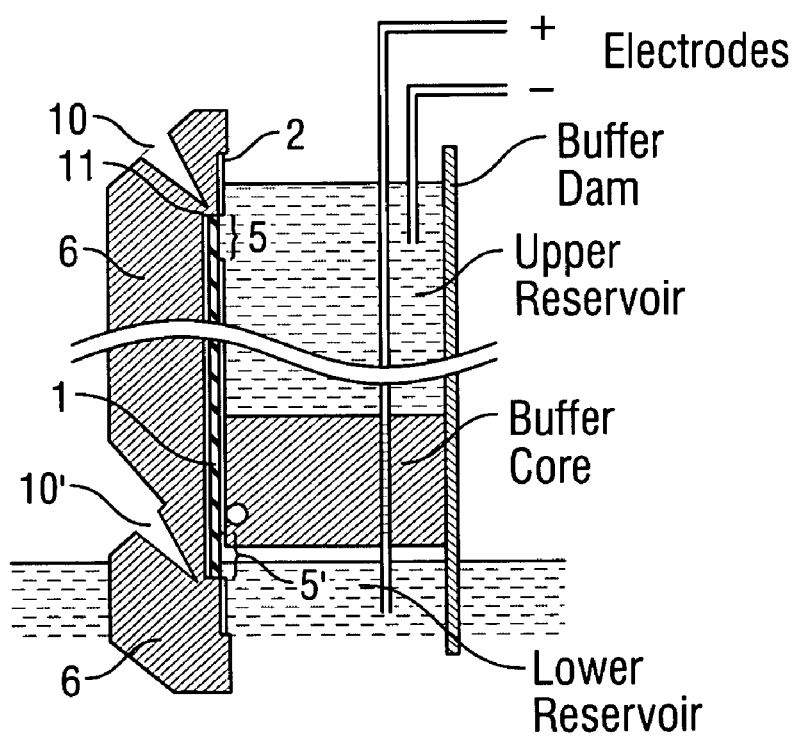
FIG. 4A is a schematic cross-sectional representation showing the arrangement of the various components used during the first dimension.

The fully loaded gel strip manifold assembly is mounted and sealed against a buffer core of the type usually found in existing mini-gel electrophoresis apparatus using the standard method provided for each brand of mini-gel electrophoresis apparatus (FIG. 4A). The slot (5) that passes through the semi-rigid backing (2) is aligned such that filling of the upper and lower electrolyte reservoirs makes electrical connections between the electrodes and the gel strip (1) inside the manifold assembly for subsequent isoelectric focusing of the gel strips.

The Second Dimension Gel Cassette and Gel Strip Transfer

Figure 3D:
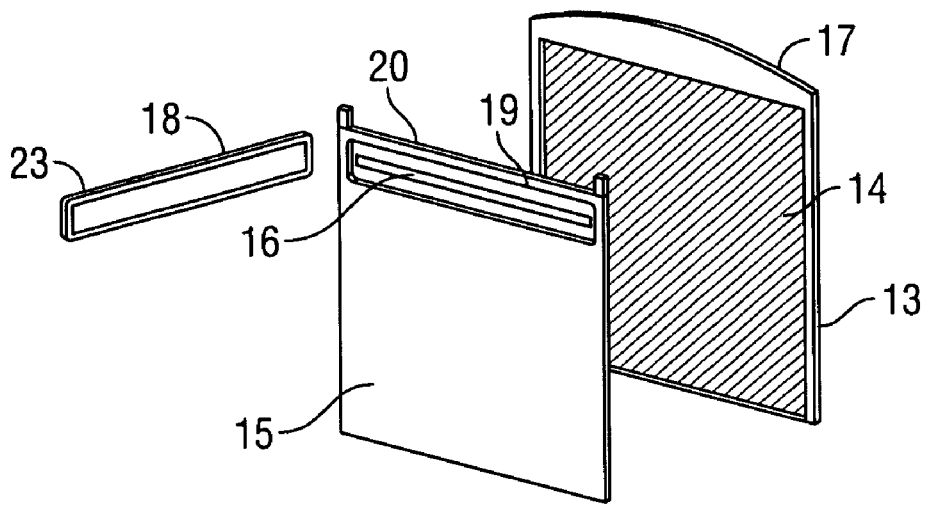
FIG. 3D is an isometric view of the second dimension gel assembly.

In a preferred embodiment, a molded cassette (13) is provided to contain a pre-cast second dimension gel which is either a uniform concentration, or pore size gradient gel (14) (FIG. 3D). Said cassette (13) is constructed of a front plate (15) that accepts the mounting of the fully focused first dimension gel strip (1) in a horizontal opening or port (16) molded into said front plate (15) of the said cassette and a back plate (17) located on the opposite face of said cassette. The said cassette is of the general size and design of existing pre-cast gel cassettes available from various sources that are referred to as "mini-gel cassettes". Said existing cassettes are typically around 8-10 centimeters high by about 10 centimeters wide and typically contain the pre-cast gel during polymerization by the manufacturer or end user and during subsequent use by the end user.

Said cassette (13) may be used to contain a polyacrylamide or related liquid gel solution during polymerization in which case the horizontal opening or port is temporarily sealed flush with the inside face of the front plate (15) in order to mold a uniform thickness gel. Sealing spacers (20) are also provided at the sides and bottom of the cassette to contain the gel during polymerization.

Alternatively, in another preferred embodiment, said cassette (13) may, following-polymerization in a separate molding manifold, subsequently enclose the pre-cast gel (14). Said enclosure of the pre-cast gel is accomplished by assembling the front plate (15) against the back plate (17) such that the pre-cast gel is accommodated in a correctly sized laminar space between the two plates that contains the pre-cast gel (14) without air spaces between the gel and the front plate (15) or back plate (17). The enclosure process may also seal other faces of the pre-cast gel (13) and hold the parts of the cassette together.

In this same preferred embodiment of the invention, the back plate (17) of said cassette (13) may be composed of or chemically modified on its gel facing surface with reactive moieties that will chemically bond the subsequently polymerized gel to said back plate (17) during or after said polymerization. In this case, the back plate (17) is mounted in said separate molding manifold prior to pre-casting the gel. The back plate (17) with the attached gel is then assembled, after pre-casting, with the front plate (15) to form the pre-cast gel cassette (13).

Said back plate (17) of said cassette (13) can be composed of glass or plastic materials compatible with the aqueous solutions used for polymerization and use of polyacrylamide gels. The front plate (15) can be composed of molded rigid plastic or elastomeric plastic materials suitable for molding the horizontal opening and compatible with said aqueous solutions.

The horizontal opening or port (16) molded into said front plate (15) is provided with a tight fitting elastomeric seal (18) that forms a water tight barrier in said horizontal opening (16). This elastomeric seal may be composed of the same materials as the isolating manifold (6). Said elastomeric seal provides for the attachment of the fully focused first dimension isoelectric focusing gel strip (1) on backing (2) in a tight fitting groove (19) on the side facing the second dimensional pre-cast gel (14). In a preferred embodiment, the elastomeric seal (18) is provided with a tab (23) for easy removal while submerged in place in the horizontal opening (16). The alignment of said first dimension gel strip (1) is such that said gel strip is placed in direct face to face contact with the part of the second dimension pre-cast gel (14) that is exposed through the horizontal opening (16) when the elastomeric seal is tightly fitted into said horizontal opening (16).

The mounting of the elastomeric seal (18) and attached gel-strip (1) with backing (2) into the horizontal opening (16) is performed in a manner that places said gel strip into direct contact with the second dimension pre-cast gel without entrapping or entraining air bubbles. Typically, this can be accomplished by placing one side of the flexible assembly into the opening first and pushing the remainder of the assembly down with a sliding motion from the starting end to the opposite end.

Figure 4B:
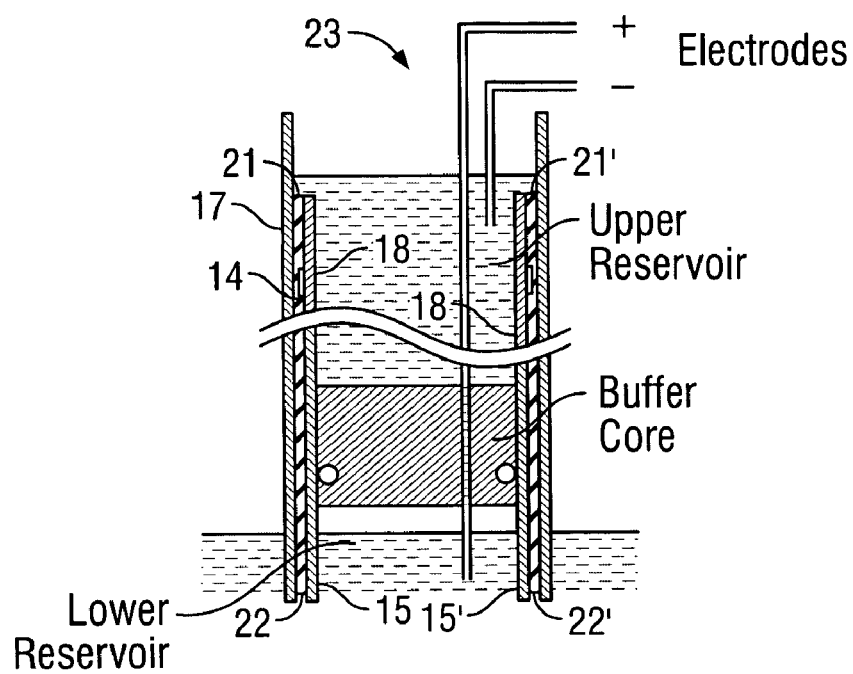
FIG. 4B is a schematic cross-sectional representation showing the arrangement of the various components used during the second dimension.

Said cassette (13), with the first dimension-gel strip (1) and elastomeric seal (18) assembly in place in the horizontal opening or port (16), is subsequently mounted and sealed against a buffer core of the type usually found in existing mini-gel electrophoresis apparatus using the standard method provided for each brand of gel electrophoresis apparatus. This assembly is lowered into the lower buffer chamber of said electrophoresis apparatus and SDS-PAGE electrolyte solutions are filled into the reservoirs. As illustrated in FIG. 4B, a lid, electrodes and a power source are attached to the electrophoresis apparatus and the second dimension gel is run so as to transfer the sample proteins from the first dimension gel strip (1) into the second dimension pre-cast gel (14) adjacent to the horizontal opening (16).

Figure 4C:
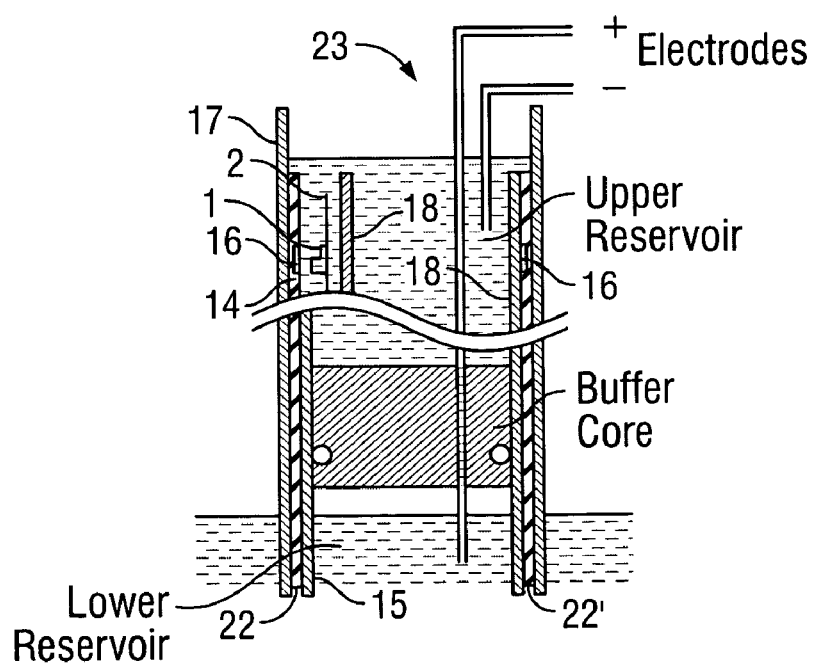
FIG. 4C is a schematic cross-sectional representation showing the arrangement of the various components used during the second dimension with the top plate and seal in a exploded view.

A current path is provided, in the typical fashion for "mini-gels", from the upper electrolyte reservoir, through the exposed and submerged top edge (21) of the >second dimension pre-cast gel (14) and out the exposed bottom edge (22) of said gel into the lower electrolyte reservoir (FIG. 4B). The lines of electrical force pass into the electrically continuous first dimension gel strip and electrophoretically mobilize the sample proteins in the strip. As shown in FIG. 4C, in a preferred embodiment, said gel strip (1) and the elastomeric seal (18) can subsequently be removed by pulling on the tab (23) after complete sample transfer from the gel strip (1) into the second dimension pre-cast gel (14) and following de-energization of the apparatus.

The removal of said gel strip (1) and elastomeric seal (18) allows the current path to run from the upper electrolyte reservoir through the now open port (16) bypassing the location of transfer and into the gel. The lower electrolyte reservoir is connected through the bottom edge of the gel (22) as before. This arrangement provides for less streaking and interference from residual non-transferred sample components located on the surface of the second dimension pre-cast gel (14) and is generally known to be beneficial.

In an alternate embodiment of the present invention, the front plate (15) is assembled onto a separately polymerized pre-cast gel (14) to form the cassette (13), and said front plate (15) is constructed of elastomeric materials of the same type as described for the isolating manifold (6), the use of the elastomeric seal (18) as a means of aligning the first dimension gel strip (1) can be eliminated.

In this alternate embodiment, the front plate (15) has the horizontal opening and a groove to accept the semi-rigid gel strip backing plate (2) both molded into the front face of the front plate opposite the side that faces the second dimension pre-cast gel (14). The fully focused and separated first dimension gel strip (1) on its semi-rigid backing (2) is mounted directly in the horizontal opening or port (16) in the same fashion as the elastomeric seal is mounted in the previous embodiment of the invention so as to prevent entrapment or entrapment of air bubbles.

The following is a step by step example of how the preferred embodiment of the present invention can be used.

EXAMPLE 1

Step 1: Mount Dehydrated Strips On Manifold

Figure 5A:
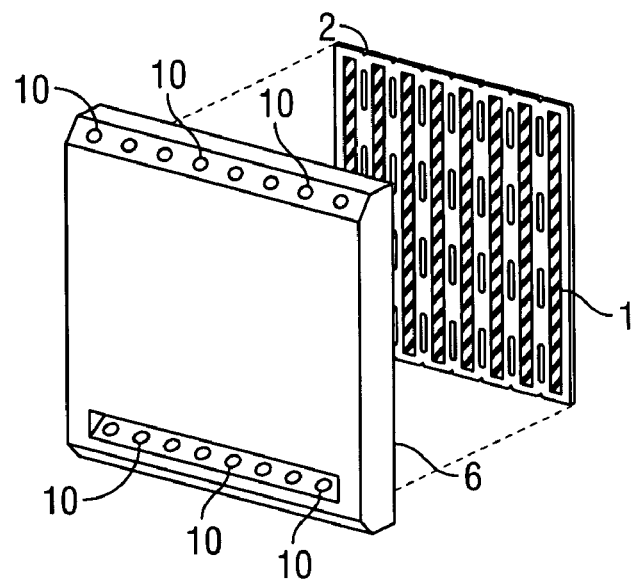
FIG. 5A is a schematic representation showing the mounting of the pre-cast strips on the manifold.

FIG. 5A shows partially dehydrated pre-cast polyacrylamide pH gradient gel strips (1), bound to a perforated plastic backing (2) at 9.0 millimeter spacing, are pressed into molded channels (8) on one side of an elastomeric manifold (6) so that each strip is sealed with a laminae space above the gel. Each laminar space is accessible for filling through two normally closed diagonal ports, top and bottom on the opposite side of the elastomeric manifold from the strips.

Step 2: Load Samples

Figure 5B:
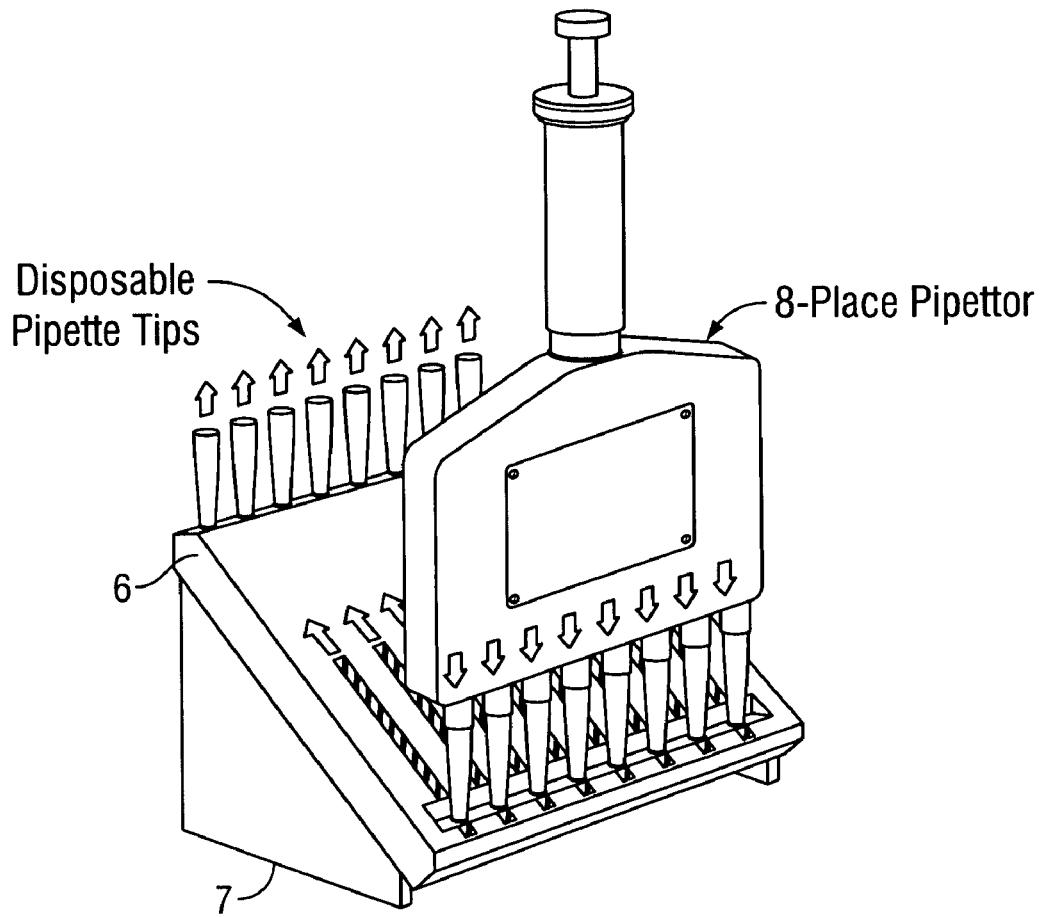
FIG. 5B is a schematic representation showing the loading of samples onto the gel strips on the manifold.

FIG. 5B shows how the elastomeric manifold (6) is mounted at an angle on the diagonal support stand (7). Samples containing proteins to be focused are loaded through the bottom ports (10), pushing open the collapsible channels (11) and filling the laminae space above each strip. Sample loading is most easily accomplished using an 8-place pipettor. Sets of disposable pipette tips are first inserted in the top ports. The tips hold the top port (10) open through the normally closed collapsible channels (11) in order to vent the laminar space.

Step 3: Incubate to Absorb Sample into Gel

Figure 5C:
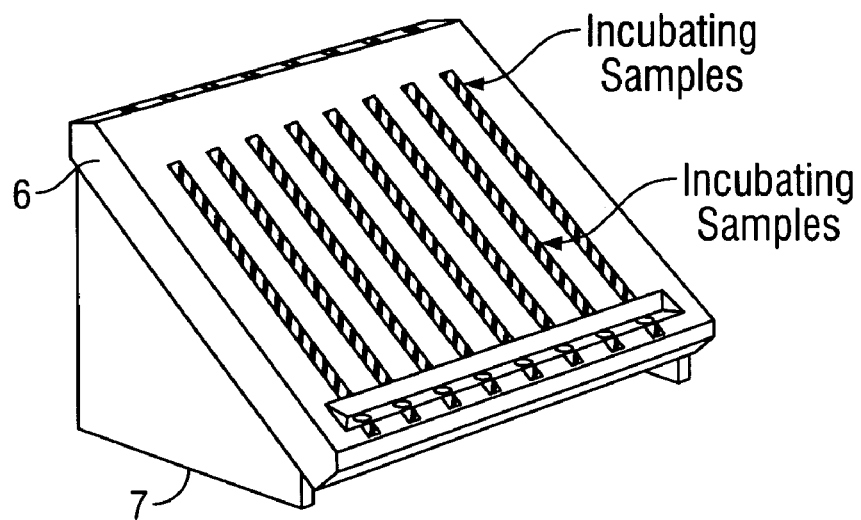
FIG. 5C is a schematic representation showing the incubation of the samples on the manifold.
Figure 5D:
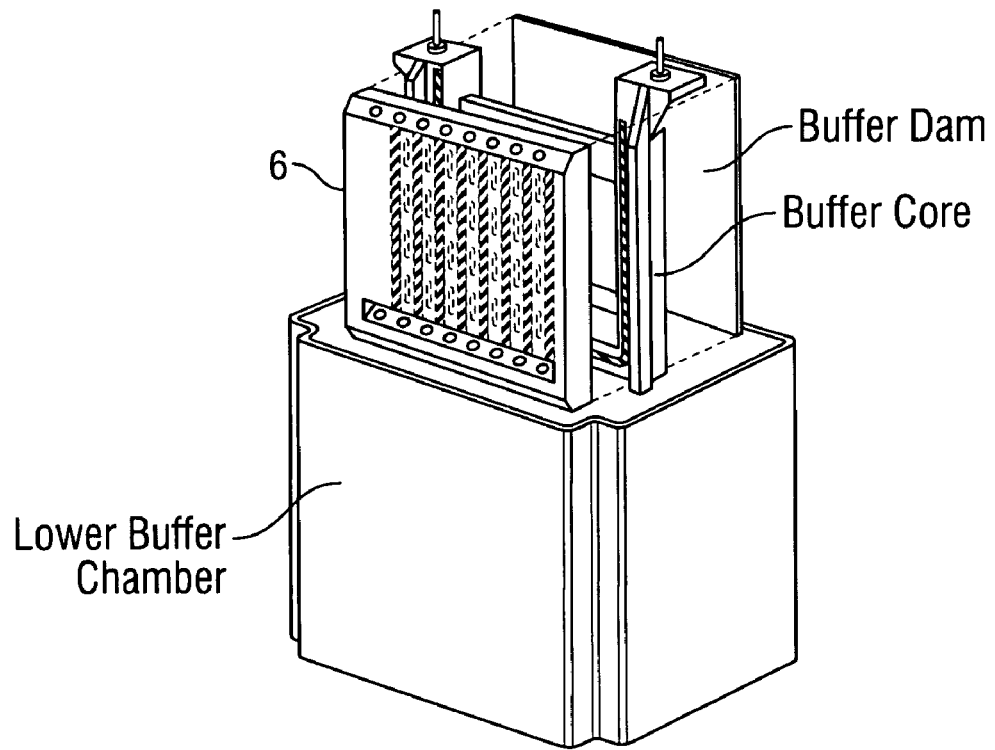
FIG. 5D is a schematic representation showing the attachment of the manifold to the buffer core assembly.

FIG. 5C shows that as the pipette tips are removed, the ports (10) in the elastomeric material reclose the collapsible channels (11) to seal the laminar space containing each sample. During an incubation lasting several hours, the samples will re-hydrate into the isoelectric focusing strips and be absorbed along with other reagents such as detergents and urea. After Rehydration is complete, the entire assembly is ready for the first dimension isoelectric focusing step.

Step 4: Place Manifold Against the Buffer Core

Any excess fluid in the laminar space is removed with a pipette. The manifold (6), with as many as eight attached sample loaded isoelectric focusing strips, is mounted on the "mini-gel" buffer core and sealed. A buffer dam or second manifold is installed on the opposite side and the assembly is dropped into the lower buffer chamber of the apparatus. Electrolyte is added to the reservoirs to levels above the connecting slots (5) that have been punched through the perforated plastic backing (2) at the top and the bottom of each gel strip. This conductivity path allows the isoelectric focusing gel to be electrically connected to the reservoirs.

Step 5: Run First Dimension Gel

The cell is attached to a constant voltage power supply and run for about an hour at low voltage to load the samples into the focusing gel. The voltage is then increased to complete isoelectric focusing over a convenient run time.

Step 6: Re-Equilibrate Strips for SDS PAGE

Figure 5E:
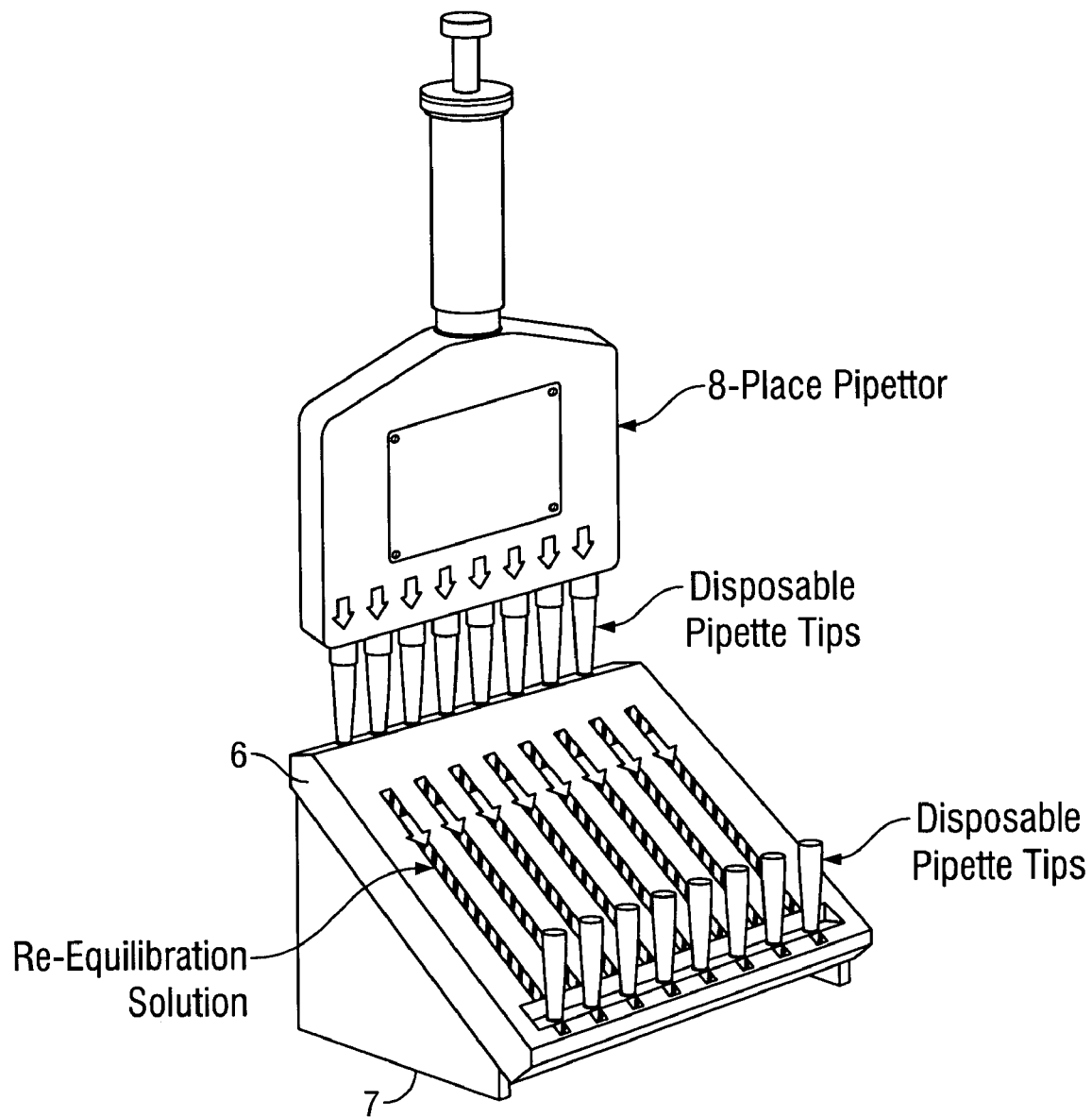
FIG. 5E is a schematic representation showing the addition of re-equilibration solution to the samples on the manifold.

FIG. 5E shows that at the end of the first dimension isoelectric focusing run, the manifold (6) is either quickly frozen for latter use or remounted on the support stand. Re-equilibration solution containing SDS detergent, and DTT is filled into the laminar spaces to denature and reduce the proteins in the strip. The reagents flow by gravity from the upper ports to the lower ports (10). They may be refilled as needed. The SDS denatured gels are then removed from the manifold ready to separate into individual strips and apply to the second dimension gel.

Step 7: Separate the Gel Strips (Steps 7-10 are Depicted in FIG. 5F)

Figure 5F:
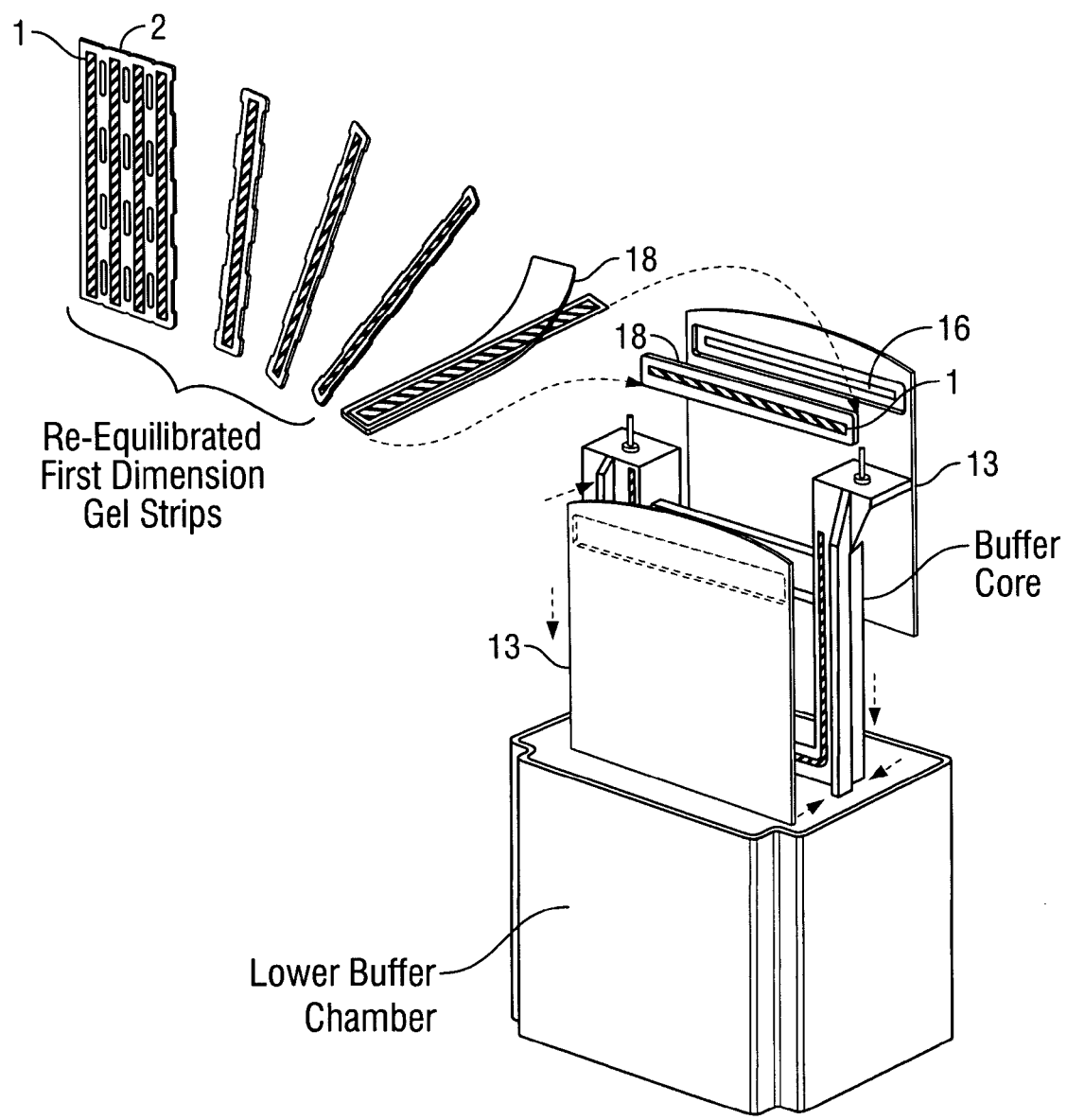
FIG. 5F is a schematic representation showing the disassembly/separation of the equilibrated gel strips in preparation for second dimension electrophoresis and the separated gel strips being placed in the second dimension electrophoresis cassette.

FIG. 5F shows that re-equilibrated first dimension gel strips (1) are quickly snapped apart and each is press mounted in a molded groove of the elastomeric seal (18) with the gel side of the strip facing out.

Step 8: Apply to Second Dimension

The first dimension strip (1) and seal (18) are carefully pressed into a slot (16) in the side of the second dimension gel cassette (13) by starting at one end so as to make face to face contact with the exposed surface of the second dimension polyacrylamide gel in the cassette slot.

Step 9: Transfer Proteins

The gel cassettes are pressed against the buffer core, sealed and dropped into the lower buffer chamber. The buffer core and lower buffer chamber are filled with electrolyte solution and the system is energized during the migration of proteins out of the strip.

Step 10: Complete Second Dimension Separation

After all the focused proteins have migrated into the second dimension gel, the power is interrupted and the first dimension strip and elastomeric seal are removed. The power is reset for the remainder of the run with the current path now running through the slot in the side of the cassette. Following completion of the second dimension, the gels are removed and stained or transblotted.

Although the invention has been described above in detail for the purpose of illustration, it is understood that numerous variations and alterations may be made by the skilled artisan without departing from the spirit and scope of the invention defined by the following claims.

What is claimed:

1. A vertical electrophoresis system comprising:
an electrophoresis chamber,
a buffer core positioned within the electrophoresis chamber; and
a cassette sealed to said buffer core, said cassette comprising a plurality of parallel channels enclosing a plurality of semi-rigid supports and a plurality of pH gradient gels, wherein to one face of each of said semi-rigid supports is covalently attached a pH gradient gel of the plurality of pH gradient gels, wherein each said gel is sealed and isolated from the other gels in a separate laminar space of a channel of the plurality of parallel channels;
wherein each said channel comprises a port at the bottom and top of each laminar space for loading of sample.

2. The cassette of claim 1, wherein said pH gradient gels are isoelectric focusing gels.

3. The cassette of claim 1, wherein said cassette is from about 8 to about 10 cm high and about 10 cm wide.

4. The cassette of claim 1, wherein said pH gradient gels are gel strips.

5. The cassette of claim 1, wherein said space is from about 4 to about 6 mm wide.

6. The cassette of claim 1, wherein said pH gradient gels are precast disposable gels.

7. The cassette of claim 1, wherein said pH gradient gels are tube gels.

8. The cassette of claim 4, wherein said gel strips are from about 3 to about 5 mm wide.

9. The cassette of claim 4, wherein said gel strips have a length of from about 80 to about 120 mm.

10. The cassette of claim 4, wherein said gel strips have a thickness when fully hydrated of from about 0.2 to about 1.0 mm.

11. The cassette of claim 1, wherein said vertical electrophoresis apparatus is a mini-gel electrophoresis apparatus.

12. A vertical electrophoresis apparatus comprising:
a buffer core; and
a gel strip-manifold assembly sealed to said buffer core, wherein said manifold assembly comprises:
a plurality of semi-rigid supports, wherein to one face of each of said semi-rigid supports is covalently attached each of a plurality of gel strips, wherein the plurality of gel strips are arranged in parallel with a space between them; and
an isolating manifold, comprising a plurality of parallel channels,
wherein each of said gel strips is enclosed by a channel of the plurality of parallel channels and sealed and isolated from the other gel strips in a separate laminar space, wherein each said laminar space is defined by the channel enclosing the strip, wherein each said channel comprises a port at the bottom and top of each laminar space for loading of sample.

13. The gel strip-manifold assembly of claim 12, wherein said gel strips are isoelectric focusing gels.

14. The assembly of claim 12, wherein said isolating manifold comprises an elastomeric material.

15. The gel strip-manifold assembly of claim 12, wherein said space is from about 4 to about 6 mm wide.

16. The gel strip-manifold assembly of claim 12, wherein said gel strips are precast on said semi-rigid support.

17. The gel strip-manifold assembly of claim 12, wherein said gel strips are from about 3 to about 5 mm wide.

18. The gel strip-manifold assembly of claim 12, wherein said gel strips have a length of from about 80 to about 120 mm.

19. The gel strip-manifold assembly of claim 12, wherein said gel strips have a thickness when fully hydrated of from about 0.2 to about 1.0 mm.

20. The apparatus of claim 12, wherein said apparatus is a mini-gel electrophoresis apparatus.

* * * * *